(12) United States Patent
Dybro et al.

(10) Patent No.: US 9,832,928 B2
(45) Date of Patent: Dec. 5, 2017

(54) CROP SENSING

(71) Applicant: Deere and Company, Moline, IL (US)

(72) Inventors: Niels Dybro, Sherrard, IL (US); Larry L. Hendrickson, Savoy, IL (US)

(73) Assignee: Deere & Company, Moline, IL (US)

( * ) Notice: Subject to any disclaimer, the term of this patent is extended or adjusted under 35 U.S.C. 154(b) by 740 days.

(21) Appl. No.: 14/184,056

(22) Filed: Feb. 19, 2014

(65) Prior Publication Data

US 2014/0230396 A1 Aug. 21, 2014

Related U.S. Application Data

(63) Continuation of application No. 13/771,682, filed on Feb. 20, 2013.

(51) Int. Cl.
| | |
|---|---|
| *G01L 19/08* | (2006.01) |
| *A01D 45/02* | (2006.01) |
| *G01G 19/00* | (2006.01) |
| *G01L 1/00* | (2006.01) |
| *G01N 33/24* | (2006.01) |
| *G01N 33/00* | (2006.01) |
| *A01D 41/127* | (2006.01) |
| *G01L 5/00* | (2006.01) |
| *G01G 19/12* | (2006.01) |

(52) U.S. Cl.
CPC ......... *A01D 45/021* (2013.01); *A01D 41/127* (2013.01); *G01G 19/00* (2013.01); *G01L 1/00* (2013.01); *G01L 5/0061* (2013.01); *G01N 33/0098* (2013.01); *G01N 33/24* (2013.01); *G01G 19/12* (2013.01)

(58) Field of Classification Search
CPC ......... A01D 41/127; G01G 19/00; G01L 1/00
USPC .................................... 73/865, 865.8, 272 R
See application file for complete search history.

(56) References Cited

U.S. PATENT DOCUMENTS

| | | |
|---|---|---|
| 4,527,241 A | 7/1985 | Sheehan et al. |
| 4,598,535 A | 7/1986 | Sousek |
| 5,216,483 A | 6/1993 | Berthold et al. |
| 5,220,172 A | 6/1993 | Berthold et al. |
| 5,282,389 A | 2/1994 | Faivre et al. |
| 5,486,915 A | 1/1996 | Jeffers et al. |
| 5,680,750 A | 10/1997 | Stefl |
| 5,790,428 A | 4/1998 | Easton |
| 5,789,741 A | 8/1998 | Kinter et al. |
| 5,793,035 A | 8/1998 | Beck et al. |
| 5,995,894 A | 11/1999 | Wendte |
| 6,061,618 A | 5/2000 | Hale et al. |

(Continued)

FOREIGN PATENT DOCUMENTS

| | | |
|---|---|---|
| WO | WO2006063314 | 6/2006 |
| WO | 2011063814 A | 6/2011 |
| WO | WO2013023142 | 2/2013 |

OTHER PUBLICATIONS

International Search Report for PCT/US2014/017087 dated Jun. 10, 2014.

(Continued)

*Primary Examiner* — Peter Macchiarolo
*Assistant Examiner* — Alexander Mercado
(74) *Attorney, Agent, or Firm* — Rathe Lindenbaum LLP

(57) ABSTRACT

A crop harvesting width of a harvester head is partitioned into a plurality of portions. At least one sensor detects a metric of a crop being harvested for each of the plurality of portions. A processing unit determines an attribute of the crop harvested for each of a plurality of portions using the detected metric.

19 Claims, 9 Drawing Sheets

(56) References Cited

U.S. PATENT DOCUMENTS

| | | |
|---|---|---|
| 6,119,442 A | 9/2000 | Hale |
| 6,178,253 B1 | 1/2001 | Hendrickson et al. |
| 6,389,884 B1 | 5/2002 | Diekhans et al. |
| 6,460,260 B1 | 10/2002 | Alster |
| 6,475,081 B2 | 11/2002 | Coers et al. |
| 6,551,451 B2 | 4/2003 | Trung et al. |
| 6,584,390 B2 | 6/2003 | Beck |
| 6,592,453 B2 | 7/2003 | Coers et al. |
| 6,668,223 B2 | 12/2003 | Blackmore et al. |
| 6,738,148 B2 | 5/2004 | Dunne et al. |
| 6,806,955 B2 | 10/2004 | Jang |
| 6,839,127 B1 | 1/2005 | Anderson |
| 6,874,304 B2 | 4/2005 | Clauss |
| 6,951,514 B1 | 10/2005 | Coers et al. |
| 6,990,459 B2 | 1/2006 | Schneider |
| 6,999,877 B1 | 2/2006 | Dyer et al. |
| 7,047,133 B1 | 5/2006 | Dyer et al. |
| 7,047,135 B2 | 5/2006 | Dyer et al. |
| 7,048,627 B2 | 5/2006 | Fechner et al. |
| 7,064,810 B2 | 6/2006 | Anderson et al. |
| 7,169,040 B2 | 1/2007 | Kormann et al. |
| 7,184,892 B1 | 2/2007 | Dyer et al. |
| 7,188,450 B2 | 3/2007 | Raun et al. |
| 7,206,063 B2 | 4/2007 | Anderson et al. |
| 7,216,033 B2 | 5/2007 | Flann et al. |
| 7,228,214 B2 | 6/2007 | Flann et al. |
| 7,401,528 B2 | 7/2008 | Deppermann et al. |
| 7,412,880 B2 | 8/2008 | Barreiro et al. |
| 7,430,845 B2 | 10/2008 | Kormann et al. |
| 7,520,117 B2 | 4/2009 | Rieck et al. |
| 7,584,663 B2 | 9/2009 | Missotten et al. |
| 7,604,712 B2 | 10/2009 | Trung et al. |
| 7,694,500 B2 | 4/2010 | Arnold et al. |
| 7,702,462 B2 | 4/2010 | Fuessley et al. |
| 7,725,233 B2 | 5/2010 | Hendrickson et al. |
| 7,805,917 B2 | 10/2010 | Kempf et al. |
| 7,812,947 B2 | 10/2010 | Shakespeare et al. |
| 7,861,606 B2 | 1/2011 | Kormann |
| 7,916,898 B2 | 3/2011 | Anderson |
| 7,921,626 B2 | 4/2011 | Maertens et al. |
| 7,987,735 B2 | 8/2011 | Mann, III et al. |
| 8,049,892 B2 | 11/2011 | Shakespeare et al. |
| 8,061,114 B2 | 11/2011 | Mossman et al. |
| 8,078,367 B2 | 12/2011 | Sauder et al. |
| 2002/0117274 A1 | 8/2002 | Jang |
| 2006/0196158 A1 | 9/2006 | Faivre et al. |
| 2006/0196622 A1 | 9/2006 | Trung et al. |
| 2006/0200334 A1 | 9/2006 | Faivre et al. |
| 2007/0089390 A1 | 4/2007 | Hendrickson et al. |
| 2007/0239472 A1 | 10/2007 | Anderson |
| 2007/0288167 A1 | 12/2007 | Anderson et al. |
| 2007/0294994 A1 | 12/2007 | Deppermann et al. |
| 2009/0118910 A1 | 5/2009 | Carr et al. |
| 2009/0282794 A1 | 11/2009 | Wilcox |
| 2010/0063673 A1 | 3/2010 | Anderson |
| 2010/0089176 A1 | 4/2010 | Mann, III et al. |
| 2010/0089178 A1 | 4/2010 | Tragesser et al. |
| 2010/0250482 A1 | 9/2010 | Ma |
| 2010/0268679 A1 | 10/2010 | Anderson |
| 2011/0011048 A1 | 1/2011 | Hoffman |
| 2011/0146218 A1 | 6/2011 | Carboni |
| 2011/0153136 A1 | 6/2011 | Anderson |
| 2011/0173942 A1 | 7/2011 | Kowalchuk |
| 2012/0029757 A1 | 2/2012 | Kowalchuk |
| 2012/0029761 A1 | 2/2012 | Anderson |
| 2012/0050023 A1 | 3/2012 | Sauder et al. |
| 2014/0002489 A1 | 1/2014 | Sauder et al. |

OTHER PUBLICATIONS

B.K. Gibson, C.D. Parker & F.R. Musser, Corn Stalk Penetration Resistance as a Predictor of Southwestern Corn Borer (Lepidoptera: Crambidae) Survival, MidSouth Entomologist, 2009, vol. 3, 7-17, Missippi, www.midsouthentomologist.org.msstate.edu.

Croplan, Stalk Quality, Corn Expertise, 2010, 3 pages, http://www.croplangenetics.com/FINDSEED/CORN/ECMD014194.aspx.

D.D. Bochtis, C.G. Sorensen, & O. Green, Soil Compaction Reduction System (SOCRESY REPORT) Presentation, University of Aarhus, Faculty of Agricultural Sciences, Department of Biosystems Engineering, May 18, 2011, 17 pages, Denmark.

D.D. Bochtis, C.G. Sorensen, & O. Green, Soil Compaction Reduction System (SOCRESY REPORT), University of Aarhus, Faculty of Agricultural Sciences, Department of Biosystems Engineering, May 18, 2011, 17 pages, Denmark.

Dirk Vandenhirtz, High throughput plant phenotyping for the development of better plants for the future, LemnaTec Presentation from Oct. 27, 2010, 102 pages.

Duli Zhao, K. Raja Reddy, V. Gopal Kakani, John J. Read & Sailaja Koti, Canopy reflectance in cotton for growth assessment and lint yield prediction, ScienceDirect, Dec. 19, 2006, (26) 335-344, European Journal of Agronomy.

James C. Frisby & Donald L. Pfost, Soil Compaction: The Silent Theif, University of Missouri Extension, Department of Agricultural Engineering, Oct. 1993, 4 pages, http://extension.missouri.edu/p/G1630.

Jonathan P. Kelly, By-plant prediction of corn (Zea mays L.) grain yield using height and stalk diameter, ProQuest, Dec. 2011, 2 pages, Oklahoma State University, http://proquest.umi.com/pqdlink?did=2401960911&Fmt=7&clientId=79356&RQT=309&VName=PQD.

Lei Zhang & Tony E. Grift, A monocular vision-based diameter sensor for Miscanthus giganteus, ScienceDirect, Jan. 21, 2012, 298-304, Illinois, www.elsevier.com/locate/issn/15375110.

MDL Laser Systems, LaserAce HypsoMeter Simple "All in One" Heighting, Diameter & Log Volume Instrument with Data Storage, 02 May 22, 2006, Western Data Systems, Inc., www.laserace.com.

Peter Tittmann, Sohail Shafii, Bruce Hartsough, Bernd Hamann, Tree Detection and Delineation from LiDAR point clouds using RANSAC, SilviLaser, Oct. 16-19, 2011, Department of Geography, UCD, 23 pages.

Salas, Ene, Gregoire, Naesset & Gobakken, Modelling tree diameter from airborne laser scanning derived variables: A comparison of spatial statistical models, Elsevier Ltd., 2010, 5 pages, http://pubget.com/paper/pgtmp_8001e8721eb6c97b19ea68023001f58e/Modelling_tree_diameter_from_airborne_laser_scanning_derived_variables_A_comparison_of_spatial_statistical_models.

Sorin C. Popescu, Randolph H. Wynne & Ross F. Nelson, Measuring Individual Tree Crown Diameter With Lidar and Assessing Its Influence on Estimating Forest Volume and Biomass, Canadian Journal of Remote Sensing, vol. 29, No. 5, 564-577, 2003.

Steve Watson, Drought-stressed corn needs timely harvest to avoid stalk lodging, CNHI, www.farmtalknewspaper.com, Sep. 7, 2011, 2 pages,, http://farmtalknewspaper.com/crops/x1642542647/Drought-stressed-corn-needs-timely-harvest-to-avoid-stalk-lodging.

Thomas Hellstrom, Peter Hohnloser, Ola Ringdahl, Tree Diameter Estimation Using Laser Scanner, Department of Computing Science Umea University, Dec. 20, 2012, 15 pages, Umea Sweden.

University of Kentucky, Producers Should Check Corn's Stalk Strength Before Harvest, Crop Management, University of Kentucky Press Release, 1 page, Sep. 21, 2009, http://www.plantmanagementnetwork.org/pub/cm/news/2009/StalkStrength/.

University of Wisconsin Madison, Precision Agriculture Precision Modeling, 2003, 2 pages, Madison, Wisconsin, http://www.soils.wisc.edu/~norman/RESAC/agric/modeling.html.

Unknown, Improved System and Method for Controlling Agricultural Vehicle Operation Using Historical Data, unknown, 7 pages.

International Search Report for PCT/US14/12419 dated May 16, 2014.

International Search Report for PCT/US2014/011849 dated May 9, 2014.

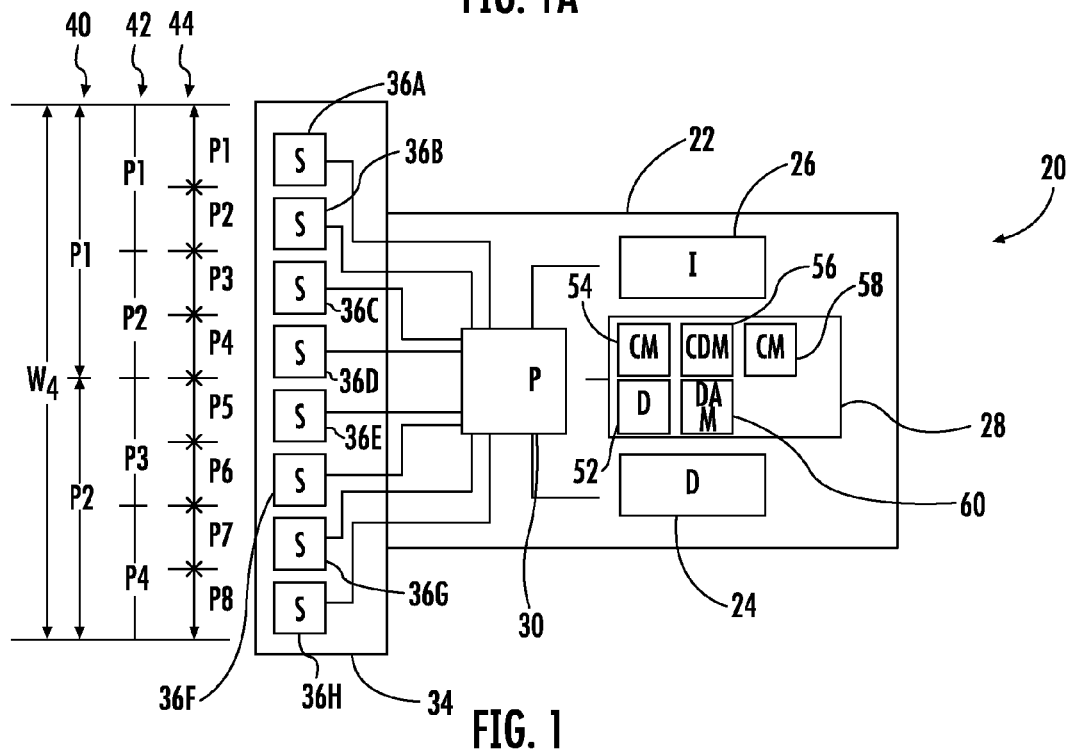
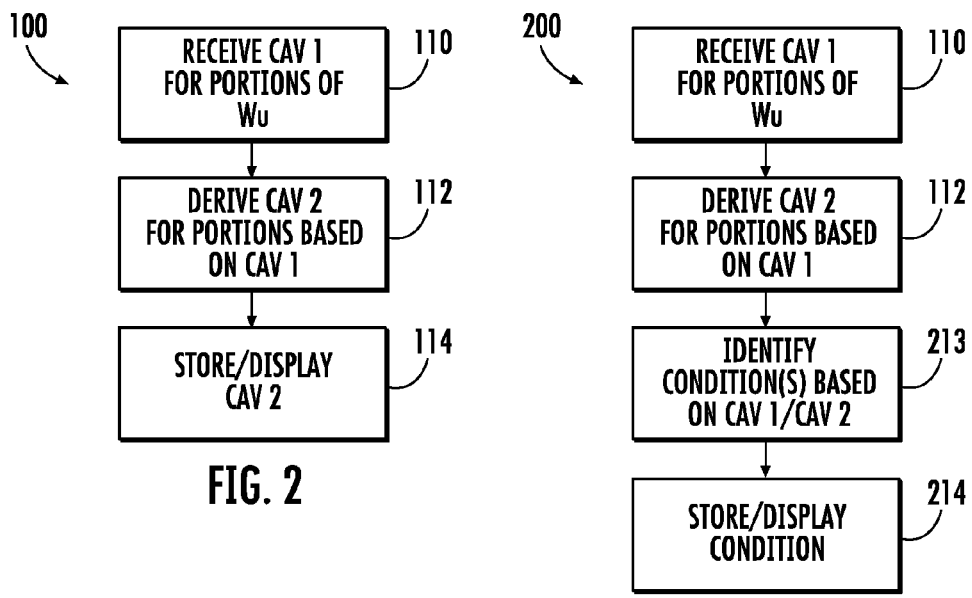

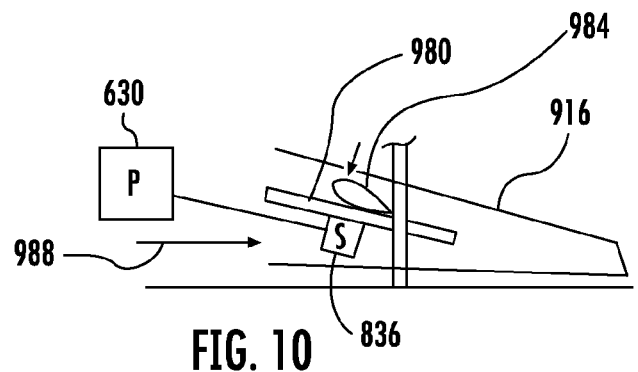
FIG. 10
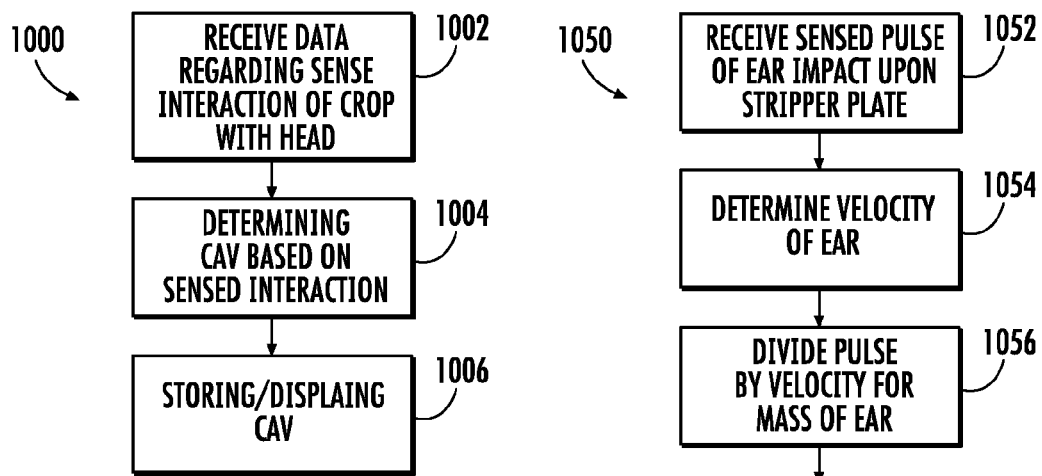
FIG. 11
FIG. 12

CROP SENSING

CROSS-REFERENCE TO RELATED PATENT APPLICATIONS

The present application is a continuation application claiming priority under 35 USC Section 120 from the pending U.S. patent application Ser. No. 13/771,682 filed on Feb. 20, 2013 and entitled CROP SENSING, the full disclosure of which is hereby incorporated by reference. The present application is related to co-pending U.S. patent application Ser. No. 13/771,727 filed on Feb. 20, 2013 and entitled PER PLANT CROP SENSING RESOLUTION, the full disclosure of which is hereby incorporated by reference. The present application is related to co-pending U.S. patent application Ser. No. 13/771,760 filed on Feb. 20, 2013 and entitled CROP SENSING DISPLAY, the full disclosure of which is hereby incorporated by reference. The present application is related to co-pending U.S. patent application Ser. No. 13/771,795 filed on Feb. 20, 2013 and entitled SOIL COMPACTION REDUCTION SYSTEM AND METHOD, the full disclosure of which is hereby incorporated by reference.

BACKGROUND

Crop harvesting machines, such as combines, sometimes include crop throughput sensors. Such sensors detect the ongoing crop yield of the swath of the harvesting machine. The information produced from such sensors may be inadequate for the ever-increasing sophistication of crop management.

BRIEF DESCRIPTION OF THE DRAWINGS

FIG. 1 is a schematic illustration of an example crop sensing system.

FIG. 1A is a schematic illustration of a portion of the crop sensing system of FIG. 1.

FIG. 2 is a flow diagram of an example method that may be carried out by the crop sensing system of FIG. 1.

FIG. 3 is a flow diagram of another example method that may be carried out by the crop sensing system of FIG. 1.

FIG. 10 is a schematic illustration illustrating the sensing of one or more crop attributes by the system of FIG. 9.

FIG. 11 is a flow diagram illustrating an example method that may be carried out by the crop sensing system of FIG. 9.

FIG. 12 is a flow diagram illustrating another example method that may be carried out by the crop sensing system of FIG. 9.

DETAILED DESCRIPTION OF THE EXAMPLE EMBODIMENTS

Figure 4:
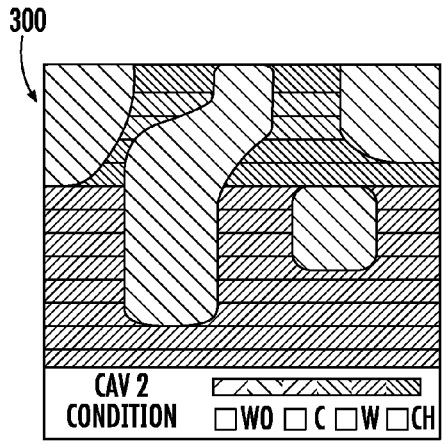
FIG. 4 is a diagram of an example field map that may be generated by the crop sensing system of FIG. 1 carrying out the method of FIG. 3.

FIG. 1 schematically illustrates an example crop sensing system 20. Crop sensing system 20 outputs crop data and field maps with an enhanced resolution. In an example embodiment, the term "resolution" refers to the level of detail with regard to crop data and/or field maps. Resolution for crop data or field maps is determined by the smallest unit for which an attribute is sensed or for which an attribute is derived. Generally, the smaller the unit, the greater the resolution. Crop sensing system 20 outputs crop data and maps a field using sensed or derived attributes and/or identified conditions for individual units or portions of the field having a width less than a utilized crop harvesting width of a harvester. For example, even though a harvester may have a harvesting swath of 12 rows, crop sensing system 20 may output crop data or field maps providing crop attributes such as, yield, for less than 12 rows, such as on a row-by-row basis or even a plant-by-plant basis. Crop sensing system 20 may be similarly implemented with respect to non-row crops and non-row harvesters. The greater crop data resolution provided by crop sensing system 20 facilitates more advanced and sophisticated crop management.

Crop sensing system 20 comprises an agricultural machine, an example of which is the illustrated harvester 22. Crop sensing system 20 further comprises display 24, input 26, processor 30 and memory 28. Harvester 22 comprises a mobile machine configured to travel across a field or plot of land while harvesting a crop. Harvester 22 comprises head 34 and sensors 36A-36H (collectively referred to as sensors 36). In other implementations, crop sensing system 20 may comprise other types of agricultural machines. Other examples of an agricultural machine are planters, cultivators, herbicide, insecticide or fertilizer applicators, cutters, mowers, pruners and/or the like.

Head 34 comprises a mechanism configured to gather and harvest a crop along a swath. The swath of head 34 has a utilized width, Wu, when harvesting crops. In an example embodiment, the utilized width Wu constitutes that portion of the length or swath width that is being utilized to harvest crops at a particular time. Although in most instances, the utilized width Wu is equal to the physical length of the swath of head 34, in some circumstances, the utilized width Wu may constitute only a portion of the swath of head 34, such as along an end row, waterway and/or the like. Head 34 includes various mechanisms for harvesting, such as mechanisms to sever or separate the crop from a remainder of a plant. Such mechanisms may include knives or blades, stripper plates, rollers, snapping roles, augurs, gathering chains or belts and/or the like. In one implementation, head 34 may comprise a corn head for a combine, wherein the corn head separates ears of corn from the remaining stalk. In another implementation, head 34 may comprise a grain head for a combine, wherein the grain along with the stalk is severed and subsequently threshed by the combine. In other implementations, head 34 may have other configurations.

For example, although head 34 is illustrated as being located at a forward end of harvester 22 and as being interchangeable with other heads (facilitating the change of corn and grain heads), in other implementations, head 34 may be supported at other locations by harvester 22 and/or may be a permanent, non-interchangeable component of harvester 22.

Sensors 36 comprise mechanisms to sense or detect one or more crop attribute values for a crop of forage plants. In one example embodiment, a forage plant comprises a poacea family or grass plant, a fabaceae family or legume plant and/or a forb plant, but excludes trees such as coniferous and deciduous trees. Examples of poaceae plants or grass plants comprise corn, rice, wheat, barley, millet, oats, sugarcane, sorghum, rye and bamboo. Examples of fabacea plants or legume plants comprise beans such as soybeans. An example of a forb comprises a sunflower plant. Sensors 36 detect one or more crop attribute values for the forage plants along the entire swath of head 34 or a portion of swath or harvesting width of head 34. In one example embodiment, sensors 36 are located and carried by head 34. In one example embodiment, sensors 36 are provided in each row harvesting portion of head 34. In other implementations, sensor 36 may be provided at other locations.

Each of sensors 36 senses one more crop attribute values for crops harvested by a corresponding distinct portion of the utilized width Wu. Sensors 36 collectively detect multiple non-zero crop attribute values for a plurality of distinct portions of the utilized width Wu. Said another way, each of sensors 36 senses only a portion of the total crop being harvested at any moment in time by head 34, wherein each of sensors 36 provide crop attribute values for just that portion. For example, in one embodiment, each of sensors 36 may cents a crop attribute for plants along an individual row, providing "per row" crop attributes.

For example, as shown by FIG. 1, in one circumstance, the entirety of head 34 may be receiving and harvesting crops such that the utilized width Wu of head 34 is substantially equal to the physical width or swath of head 34. Sensors 36 each detect a less than whole portion or a fraction of the crop being harvested by the utilized width Wu. In one implementation, as indicated by partitioning 40, the utilized width Wu may be partitioned or divided into two equal portions P1 and P2, wherein sensors 36A-36D provide a first crop attribute value for crops received by portion P1 while sensors 36E-36H provide a second crop attribute value for crops received by portion P2. In another implementation, as indicated by partitioning 42, the utilized width Wu may be partitioned or divided into four equal portions P1, P2, P3 and P4, wherein sensors 36A-36 B, sensors 36C-36D, sensors 36E-36F and sensors 36G-36H provide independent and distinct crop attribute values for crops received by portions P1-P4, respectively. In yet another implementation, as indicated by partitioning 44, the utilized width Wu may be partitioned or divided into 8 equal portions P1-P8, wherein sensors 36A-36H each provide a distinct crop attribute value for crops received from portions P1-P8, respectively.

Although the individual portions of partitionings 40 and 42 are each illustrated as being associated with multiple sensors, in other implementations, each of the portions of partitionings 40 and 42 may alternatively be associated with a single sensor or with other numbers of sensors. Although head 34 is illustrated as including eight sensors, in other implementations, head 34 may include a greater or fewer number of such sensors along the physical width or swath of head 34. For example, a crop row harvester may have greater than or less than eight rows, wherein the head of the harvester may similarly divide with greater than or less than eight row sensing sensors. Although head 34 is illustrated as being partitioned into equal portions, in other example embodiments, head 34 is partitioned into unequal portions, wherein sensors sense crop attributes for the unequal portions. For example, in another implementation, one of sensors 36 senses or detects crop attributes for an individual row while another center 36 senses crop attributes for a plurality of rows.

As shown by FIG. 1, in some implementations, each of sensors 36 may offer an even higher degree of crop sensing resolution by being configured to detect crop attribute values for the individual plants 46 themselves. In some implementations, the sensed crop attribute values for individual plants 46 may be aggregated into sets or collections 48 of plants based upon time, distance, a number of plants, and/or the like to reduce the amount of data that is processed or stored. Aggregating individual plant data may also improve useability of the data by eliminating noise in the data. The sensed crop attribute values for the individual plants 46 comprise values which are independent of, or do not merely comprise the presence or location of the plant. Such crop attribute values for the individual plants 46 do not merely comprise data regarding the population of plants or the spacing of plants. Instead, each of sensors 36 may be configured to specifically sense other attributes of the individual plant such that crop attribute values pertaining to estimated mass of the grain or product of the individual plant, the estimated mass other than grain (MOG) of the plant and/or the like may be derived.

For example, in one implementation, each of sensors 36 senses an interaction or impact force of grain upon a portion of the head 34, such as a stripper plate of head 34, wherein a mass of the grain may be derived based upon the sensed impact force and other sensed or known values. In another implementation, sensors 36 detect a stalk thickness/diameter of an individual plant. The stalk thickness/diameter of the individual plant may be detected either through physical contact with individual plant or through laser or optical and camera-based sensors. The mass of the grain or the MOG may be derived from the sensed stalk thickness/diameter. Other examples of sensors 36 include, but are not limited to for example, light detection and ranging (LIDAR or LADAR), structured light or stereo camera vision, strain gauges, and/or accelerometers (where crop impact is sensed), and/or the like.

Display 24 comprises a device by which information may be visually presented to an operator of harvester 22 or to a remotely located monitor/manager/operator of harvester 22. Display 24 may comprise a monitor or screen which is stationary in nature or which is mobile in nature. In one implementation, display 24 is carried by harvester 22 along with the operator. In another implementation, display 24 comprises a stationary monitor remote from harvester 22. In yet other implementations, display 24 may be mobile in nature, being provided as part of a computer tablet, smart phone, personal data assistant (PDA) and/or the like.

Input 26 comprises one or more devices by which controls and input may be provided to processor 28. Examples of input 26 include, but are not limited to, a keyboard, a touchpad, a touch screen, a steering wheel or steering control, a joystick, a microphone with associated speech recognition software and/or the like. Input 26 facilitates the input of selections, commands or controls. In implementations where harvester 22 is remotely controlled or remotely steered, input 26 may facilitate such remote steering.

Memory 28 comprises a non-transient computer-readable medium or persistent storage device for storing data for use by processor 30 or generated by processor 30. In one implementation, memory 28 may additionally store instructions in the form of code or software for processor 30. The instructions may be loaded in a random access memory (RAM) for execution by processor 30 from a read only memory (ROM), a mass storage device, or some other persistent storage. In other embodiments, hard wired circuitry may be used in place of or in combination with software instructions to implement the functions described. For example, at least regions of memory 28 and processor 30 may be embodied as part of one or more application-specific integrated circuits (ASICs). In one implementation, memory 28 is carried by harvester 22. In other implementations, memory 28 may be provided remote from harvester 22.

In the example illustrated, memory 28 comprises data storage portion 52, correlation module 54, condition detection module 56, display module 58 and operations adjustment module 60. Data storage portion 52 contains historical data, such as lookup tables, facilitating analysis of data and information sensed by sensors 36. Data storage portion 52 is further configured to store the crop attribute values directly sensed by sensors 36, crop attribute values derived from the directly sensed crop attribute values using correlation module 54, crop or field conditions identified based upon the directly sensed crop attribute values and/or the derived crop attribute values. Such stored information may be in various formats such as tables, field maps and/or the like. Data storage portion 52 may additionally store various settings and operator preferences.

Correlation module 54, condition detection module 56, display module 58 and operations adjustment module 60 comprise programming, software or code for directing the operation of processor 30. Correlation module 54 instructs processor 30 in the correlation of one or more directly sensed crop attribute values detected by sensors 36 to derived crop attribute values. In other words, correlation module 54 instructs processor 30 and the derivation of crop attribute values, such as yield and/or the like, from directly sensed crop attribute values. In one implementation, correlation module 54 directs processor 30 to consult a lookup table in data storage portion 52 to correlate a stalk thickness/diameter as detected by sensors 36 to a grain mass or grain yield value, the derived crop attribute value. In another implementation, correlation module 54 directs processor 30 to carry out one or more algorithms/mathematical equations using a sensed impact of a plant or grain, and possibly using other additional factors, to derive a grain mass or yield of the plant. In other implementations, correlation module 54 directs processor 30 to derived crop attribute values from directly sensed crop attribute values in other fashions.

Condition detection module 56 directs processor 30 in the identification of field and/or crop conditions based upon the directly sensed crop attribute values or the derived crop attribute values. Examples of such field/crop conditions include, but are not limited to, the absence of plants, a field washout condition, an area of the field having yields suffering from wheel compaction beyond a predetermined threshold, the existence of a weed patch, the existence of yield loss due to inappropriate chemical application, and/or the like. In one implementation, condition detection module 56 directs processor 30 to consult a lookup table in data storage portion 52 to correlate a stalk thickness/diameter as detected by sensors 36 and/or a derived grain mass or grain yield value, the derived crop attribute value, to one of various predefined conditions, examples of which are set forth above. In another implementation, condition detection module 56 directs processor 30 to carry out one or more algorithms and/or mathematical equations using a directly sensed crop attribute value and/or a derived crop attribute value and to further compare the resulting calculation to one or more predefined thresholds to identify a field and/or crop condition. In other implementations, condition detection module 56 may direct processor 30 to identify or detect crop and/or field conditions in other fashions.

Display module 58 instructs processor 30 to generate control signals causing display 24 to present various information and/or prompts to an operator. For example, display module 58 may cause processor 30 to prompt an operator to select what partitioning 40, 42, 44 or individual plants is to be utilized, whether or not and how individual plant data is to be aggregated, how data is to be displayed (graph, chart, field map), what conditions are to be identified, how the operator is notified or alerted to such conditions, where such data is to be stored and/or the like. Display module 58 further instructs processor 30 in the display of data per operator preferences.

Operations adjustment module 60 comprises code or programming which directs processor 30 to automatically generate control signals adjusting operational parameters of harvester 22 based upon directly sensed or derived crop attribute values. In one implementation, operations adjustment module 60 generates control signals independently adjusting operational parameters of distinct portions of head 34 along its utilized width Wu. For example, operations adjustment module 60 may adjust the operational parameters of one row unit of head 34 independent of or differently with respect to another row unit of head 34 based upon directly sensed or derived crop attribute values for the crops being presently harvested by the different row units. For example, operations adjustment module 60 may, automatically in response to sensed or derived crop attribute values for crops harvested by a particular row unit, generate control signals for an actuator coupled to stripper plates of the row unit to adjust the spacing of stripper plates. This adjustment of stripper plates for the particular row unit may be independent of and different from the spacing adjustment of other stripper plates for other row units. As a result, the enhanced crop sensing resolution provides enhanced more refined control over the operation of harvester 22 to better harvest crops.

Processor 30 comprises one or more processing units configured to carry out instructions either hardwired as part of an application-specific integrated circuit or provided as code or software stored in memory 28. In the example illustrated, display 24, input 26, memory 28 and processor 30 are each illustrated as being part of and carried by harvester 22. In other implementations, one or more of such components may alternatively be located remote from harvester 22 and in communication with harvester 22 in a wireless fashion. In some implementations, some of the aforementioned functions of processor 30 in memory 28 may be shared amongst multiple processors or processing units and multiple memories/databases, wherein at least some of the processors and memories/databases may be located remote with respect to harvester 22.

FIG. 2 is a flow diagram illustrating an example method 100 that may be carried out by system 20 to sense crop harvesting. As indicated by block 110, processor 30 receives sensed crop attribute values for each of multiple portions of the utilized width Wu of head 34 of harvester 22. For example, in an implementation where partitioning 44 is employed, sensor 36A provides processor 30 with a first sensed crop attribute value for portion P1. Sensor 36B provides processor 30 with a second sensed crop attribute value for portion P2. Sensors 36C-36H similarly provide processor 30 with distinct crop attribute values for their associated portions P3-P8, respectively. In some implementations, the sensed crop attribute values may comprise a thickness or diameter of a plant stalk. In some implementations, the sensed crop attribute values may comprise an impact of a grain, such as an ear of corn, upon a portion of the head, such as a stripper plate.

As indicated by block 112, processor 30, following instructions provided by correlation module 54, utilizes the received crop attribute values (CAV 1) for each of the portions to derive a secondary crop attribute value (CAV 2) for each of the portions. In one implementation, the secondary crop attribute value CAV 2 may comprise an estimated yield. In such an implementation, processor 30 derives an estimated yield for portions that are harvesting a crop. For example, in an implementation where partitioning 44 is employed, processor 30 derives a first yield value for portion P1, the second yield value for portion P2, a third yield value for portion P3 and so on. In other implementations, other secondary crop attribute values (CAV 2), such as MOG, may be derived from the directly sensed crop attribute values CAV 1.

As indicated by block 114, processor 30 generates control signals, following the instructions contained in display module 58, to store or display the derived crop attribute values. In one implementation, processor 30 stores the derived crop attribute values in data storage portion 52 of memory 28. In one implementation, processor 30 transmits the derived secondary crop attribute values to a remote database or memory location via a wide area network, such as a wired or wireless connection. In some implementations, the root or base data, CAV 1, is also stored and/or transmitted. In some implementations, the derived secondary crop attribute values are further displayed on display 24. In some implementations, a visible or audible alert or notice may be output by display 24 in response to the derived secondary crop attribute value for a particular portion satisfying a predefined threshold. For example, if a derived crop yield for a particular portion P, such as a particular row unit of head 34, falls below a predefined threshold, the operator may be provided with an alert or notice possibly indicating problems with the operation of the particular row unit.

As noted above, because system 20 determines crop attributes for individual portions of the harvesting width, such as individual rows or individual plants (or aggregations of plants along a row), system 20 provides an operator with more detailed information having a higher resolution, allowing the operator (or the harvesting machine automatically) to make adjustments to the setting of the harvester on a row-by-row basis to adapt to different conditions that may exist on a row-by-row basis. The operator may further utilize such information to correlate the yield results for individual rows during harvest to individual row settings of other operations such as planting, tillage, fertilizer, insecticide, or herbicide application and/or the like. As a result, row-by-row settings for such other equipment operations such as planter, tillage, fertilizer, insecticide or herbicide application may be subsequently adjusted based upon the row-by-row harvesting information. For example, strip till, planters, fertilizer, insecticide, herbicide applicators and/or the like may have given rise to uneven emergence or crop development rates, wherein row level sensing information allows an operator to determine that a problem exists, to identify causes and to identify solutions prior to the next harvesting season.

Such information may also be utilized to better calibrate other crop harvesting yield estimating devices. For example, per-row yield estimates may be used with yield data captured elsewhere on the machine, such as a grain yield sensor mounted on the clean grain auger, or off the machine, such as a weigh scale at a grain storage facility. The combination of this data may be used for purposes such as sensor calibration and post-harvest data processing.

FIG. 3 is a flow diagram illustrating an example method 200 that may be carried out by system 20. As indicated by FIG. 3, method 200 comprises blocks 110 and 112 described above with respect to method 100. As indicated by block 213, processor 30, following instructions contained in condition detection module 56, utilizes the derived secondary crop attribute values and/or the directly sensed primary crop attribute values CAV 1 to identify crop and/or field conditions. For example, using the directly sensed primary crop attribute values and/or the derived secondary crop attribute values, processor 30 may identify a field condition such as yield reducing soil compaction, a wet spot, a weed patch, a washout, a yield reducing chemical application and/or the like.

Other factors may also be employed by processor 30 in identifying a crop or field condition. For example, historical planting data may be retrieved by processor 30 in making such a condition determination. In some implementations, processor 30 may additionally generate control signals causing display 24 to prompt an operator for input based upon visual inspection of the crop or field during harvest or during planting, wherein such input information may be factored into the identification of the condition by processor 30.

As indicated by block 214, processor 30 generates control signals, following the instructions contained in display module 58, to store or display the identified field/crop condition. In one implementation, processor 30 stores the identified conditions for different regions of a field or plot of land in data storage portion 52 of memory 28. In one implementation, processor 30 transmits the identified conditions to a remote database or memory location via a wide area network, such as a wired or wireless connection. In some implementations, the root or base data, CAV 1 and the derived secondary crop attribute values are also stored and/or transmitted. In some implementations, the identified conditions are further displayed on display 24. In some implementations, a visible or audible alert or notice may be output by display 24 in response to the identification of a particular condition. In some implementations, processor 30 may identify and retrieve solutions from memory 28 and may generate control signals causing display 24 to display recommended remedial action for the identified condition.

Although system 20 and methods 100, 200 have been described with respect to harvester 22, such individual row-by-row sensing may alternatively be incorporated on other vehicles or mobile machines. For example, such row-by-row sensing may be utilized on corn pickers, utilized in seed corn production, for achieving high-throughput phenotyping, allowing characterization of differential growth patterns/yields for different varieties, and/or the like. In one implementation, individual row sensors may be mounted on any vehicle providing information with regard to differential developmental rates (stalk size at different times a season). In yet other implementations, individual plant or row-row characterization may alternatively be implemented in other vehicles such as sprayers, scouting vehicles, autonomous vehicles, push carts and/or the like.

FIG. 4 is a diagram illustrating an example field map 300 that system 20 may store in storage portion 52 and/or present using display 24. Field map 300 represents an implementation of methods 100 and 200 carried out by system 20 in which both the derived secondary crop attribute values and identified conditions are mapped across a field. Field map 300 has an enhanced resolution. In the example illustrated, field map 300 has a row-by-row resolution. Field map 300 is the product of partitioning the utilized width Wu of head 34 on a row-by-row basis, wherein a metric or crop attribute of the crop being harvested is detected for each and every row unit of head 34. The different sensed metric values for the different rows of crop being harvested by the different row units of head 34 are utilized to derive the secondary crop attribute values, such as yield, for each row on a row-by-row basis. In the example shown in FIG. 4, field map 300 graphically depicts the derived secondary crop attribute values for 14 rows. As the harvester traverses the field, the sensed primary crop attribute values and the derived secondary crop attribute values (CAV 2) vary along the row. Based upon the derived secondary crop attribute values, processor 30 further detector identifies field conditions pursuant to method 200. The identified conditions are further graphically presented as part of field map 300.

Figure 5:
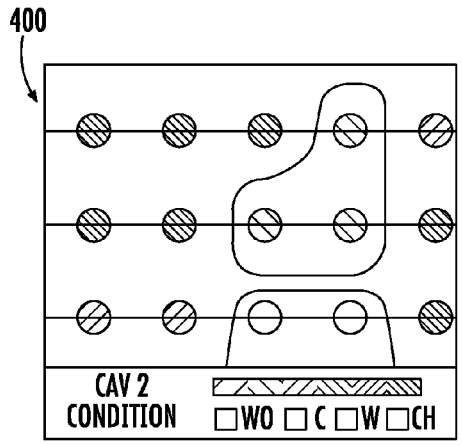
FIG. 5 is a diagram of another example field map that may be generated by the crop sensing system of FIG. 1 carrying out the method of FIG. 3.

FIG. 5 illustrates field map 400 that system 20 may store in storage portion 52 and/or present using display 24. Field map 400 represents an implementation of methods 100 and 200 carried out by system 20 in which both the derived secondary crop attribute values and identified conditions are mapped across a field. Field map 400 has an enhanced resolution. In the example illustrated, field map 400 has a plant-by-plant resolution. Field map 400 is the product of partitioning the utilized width Wu of head 34 on a row-by-row basis and distinguishing each individual plant from adjacent individual plants, wherein a metric of the crop being harvested is detected for each and every plant. In other implementations, the field map 400 may be the product of the distinguishing aggregated sets of individual plants based upon time, distance or plant count. For example, rather than processing and storing a sensed crop attribute value on a plant-by-plant basis, crop attributes may be processed and/or stored for all those plants harvested by a particular row unit during a particular period of time, for all those plants harvested as a harvester traverses a predetermined distance or for a predetermined number of plants. The different sensed metric or crop attribute values for the individual plants or aggregation of individual plants harvested by the different row units of head 34 are utilized to derive the secondary crop attribute values, such as yield, for each plant or aggregation of plants. In the example shown in FIG. 5, field map 400 graphically depicts the derived secondary crop attribute values for 15 plants. As the harvester traverses the field, the sensed primary crop attribute values and the derived secondary crop attribute values (CAV 2) vary from plant to plant. Based upon the derived secondary crop attribute values, processor 30 further detects or identifies field conditions pursuant to method 200. The identified conditions are further graphically presented as part of field map 400.

Figure 6:
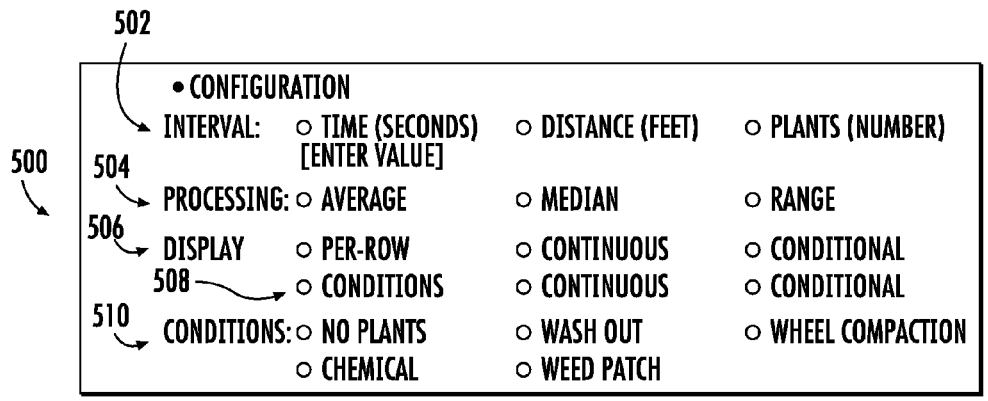
FIG. 6 is a diagram of an example configuration display screen that may be presented by the crop sensing system of FIG. 1.
Figure 7:
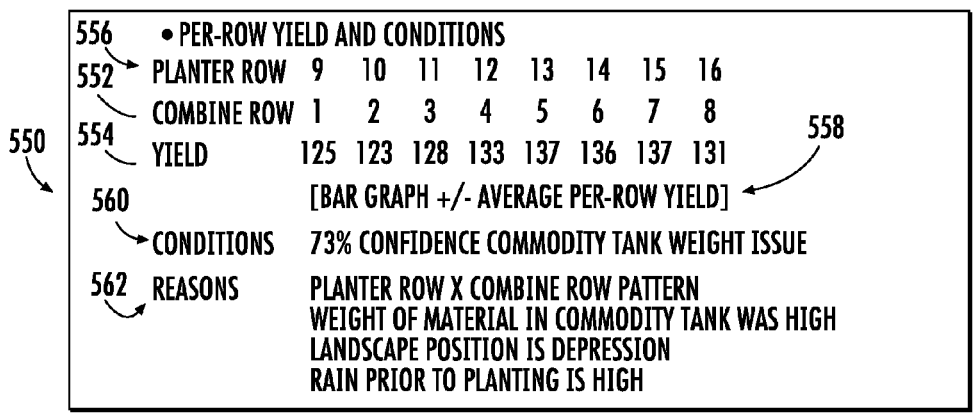
FIG. 7 is a diagram of an example output display screen that may be presented by the crop sensing system of FIG. 1.

FIGS. 6 and 7 illustrate example screen displays by display 24 under the operation of system 20. FIG. 6 illustrates an example configuration screen display 500 which may be presented on display 24 by processor 30, following instructions in display module 58. Screen display 500 presents various prompts or selections for options or modes for the configuration and operation of system 20 from which an operator may choose. As indicated by prompts 502, display 24 allows the operator to input and select the interval for which the sensed crop attributes for individual plants 46 are to be aggregated into a single data value for processing and/or storage. In the example illustrated, the operator may select from a particular time, a particular distance or a particular number of individual plants.

As indicated by prompts 504, the operator may indicate how crop attribute values for the particular interval or aggregation of individual plants are to be derived: determining an average derived crop attribute value for the aggregation of plants, determining a median value for the derived crop attribute value or a range of the derived crop attribute values.

As indicated by prompts 506, the operator is allowed to select how the derived secondary crop attribute values are displayed: whether on a continuous basis or only in response to a predefined condition being met. As indicated by prompts 508 the operator is allowed to indicate how identified conditions are presented on display 24: whether continuously displayed or only when certain conditions are identified.

As indicated by prompts 510, the operator is allowed to select which conditions are identified and which conditions are then presented on display 24 when discovered. Examples of such conditions include: no plants, wash out, wheel compaction, chemical and weed patch. In other implementations, other options or selections may be provided to the operator for the aggregation interval, the processing, the display and the conditions.

FIG. 7 illustrates an example output display screen 550 which may be presented on display 24 by processor 30, following instructions in display module 58. Screen display 550 presents the output of system 20 pursuant to the configuration selections made with respect to the screen shown in FIG. 6. As shown by data rows 552 and 554, processor 30 outputs on display 24 the derived momentary secondary crop attribute of yield for each of the eight combine rows. In other words, data rows 552 and 554 identify the momentary yield (bushels per acre) for a crop that is being harvested for each of the eight row units of head 34.

As indicated by data row 556, processor 30 further retrieves data from data storage portion 52 and correlates the particular combine rows to previously stored planter rows (the row units of the planter that planted the particular rows that are now being harvested by the harvester/combine). In some implementations, additional planting information for each of the indicated planting rows may further be retrieved from data storage portion 52 by processor 30 and presented on screen display 550. For example, different planted rows may have different values for the type or amount of applied herbicide, insecticide, or seed used in the particular row. In another example, bins containing seed and agrichemicals may have different weights in different portions of the field. As a result, the operator may be presented with information that may assist in subsequent planting by correlating different planting conditions to different yield results on a row-by-row basis. In the current example, data from planting is correlated with the per-row yield. Without limitation, data could also be drawn from past row-by-row data collection such as during tillage, spraying, scouting, land-based scouting, and aerial scouting. The data may be collected or aggregated at resolutions such as greater than field, field level, sub-field, row, and plant levels. In some embodiments, the data is geo-referenced and time-stamped to facilitate use in later analysis.

In some implementations, in addition to correlating machine-relative positions during different operations (row 3 on an 8 row combine to row 11 on a 16 row planter), system 20 may further indicate on display 550 the direction of travel of the particular mobile machine for the particular rows. For example, the direction of travel may be very beneficial when comparing processing data to tillage data where the direction of travel may be at 45° from planting and harvesting directions of travel.

As indicated by prompts 558, in addition to presenting such information in the form of a chart, system 20 further allows the operator to select other formats for presenting such information. In the example illustrated, the operator may request that such information be additionally presented as a bar graph. In other implementations, other derived crop attribute values, such as MOG, may also be displayed in the same format or other formats.

As indicated by data line 560, using the results of condition detection module 56 and following the instructions of display module 58, processor 30 presents the detected condition existing for an individual row or group of rows. In the example illustrated, processor 30 has determined, with a 73% degree of confidence, that the commodity tank weight during planting was an issue that may have resulted in soil compaction which may have resulted in lower yields for the particular rows. As indicated by portion 562, processor 30 additionally consults data storage portion 52 (or additional local or remote databases) to analyze any possible causes for the identified conditions and present such possible causes as part of screen display 550. In the example illustrated, processor 30 presents, on display 24, the various conditions that occurred for the particular set of rows, for example, the weight of the material in the commodity tank was high during planting of the particular rows, the landscape of the rows is that of a depression and that there were large amounts of rain prior to planting.

Figure 8:
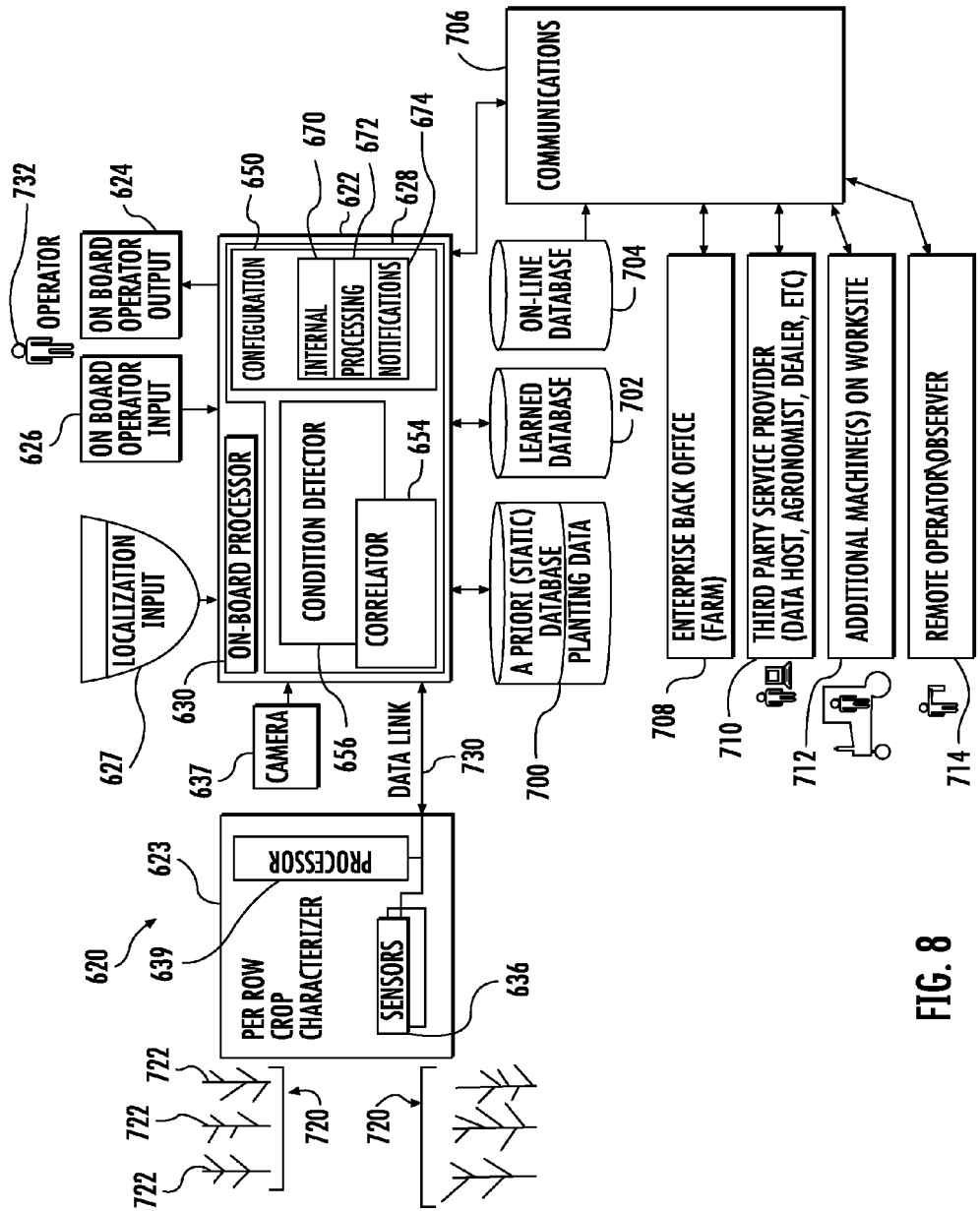
FIG. 8 is a schematic illustration of an example of the crop sensing system of FIG. 1.

FIG. 8 schematically illustrates crop sensing system 620, an example implementation of crop sensing system 20. Crop sensing system 620 comprises crop characterizer 623, on-board operator output 624, on-board operator input 626, localization input 627, memory 628, on-board processor 630, static database 700, learned database 702, online database 704, communications 706, enterprise back office 708, third-party service providers 710, other on-site machines 712 and remote operators/observers 714.

Crop characterizer 623 comprises a device configured to sense or detect multiple non-zero crop attribute values for a plurality of distinct portions of the utilized width of a harvesting machine. In the example described, crop characterizer 623 detects crop attributes or crop characteristics on at least a row-by-row basis. Individual row of crops 720 are independently sensed and different attribute values may be identified and stored for the individual rows. In the example described, crop characterizer 623 detects crop attributes on a plant-by-plant basis. Individual plants 722 are independently sensed and different attribute values may be identified and stored for the individual plants or for a predefined aggregation of individual plants along a row 720 (for example, an aggregation based upon time, distance or plant count as described above). As a result, crop characterizer 623 facilitates data gathering and field maps having an enhanced resolution for more sophisticated analysis and crop management. In one example, crop attributes are defined by crop characterizing 623 on both a plant-by-plant basis and a row-by-row basis. In another example, crop attributes are defined for a selected one of the plant-by-plant basis or the row-by-row basis.

Crop characterizer 623 comprises sensors 636 and one or more cameras 637. Sensors 636 are similar to sensors 36 described above. Sensors 636 comprise mechanisms to concurrently sense or detect one or more crop attribute values for multiple portions of a utilized crop harvesting width of the harvester. Said another way, each of sensors 636 senses only a portion of the total crop being harvested at any moment in time by the harvester 622, wherein each of sensors 636 provide crop attribute values for just that portion. As noted above, in one implementation, sensors 636 provide crop attribute values on a row-by-row basis. In another implementation, sensors 636 provide crop attribute values on a plant-by-plant basis. Such crop attribute values for the individual plants 722 do not merely comprise of data regarding the population of plants or the spacing of plants. Each of sensors 636 may be configured to specifically sense other attributes of the individual plant such that crop attribute values pertaining to estimated mass of the grain or product of the individual plant, the estimated mass other than grain (MOG) of the plant and/or the like may be derived.

For example, in one implementation, each of sensors 636 senses an interaction or impact force of grain upon a portion of the harvester, such as a stripper plate. A mass of the grain may be derived based upon the sensed impact force. In another implementation, sensors 636 detect a stalk thickness/diameter of an individual plant either through physical contact with individual plant or through non-physical contact mechanisms such as laser or optical and camera-based sensors). The mass of the grain or the MOG may be derived from the sensed stalk thickness/diameter. Examples of sensors 636 include, but are not limited to, light detection and ranging (LIDAR or LADAR), structured light or stereo camera vision, strain gauges and/or accelerometers (where crop impact is sensed).

In one implementation, camera 637 comprises an optical capture device carried by the harvester 622 to capture one or more rows 720 just prior to the harvesting of such rows 720. In one implementation, camera 637 captures images that are used to detect or determine one or more crop attributes or crop characteristics on a row-by-row basis or a plant-by-plant basis. In one implementation, camera 637 employee stereo vision or LIDAR for such detection. In one implementation, camera 637 captures images of the crop prior to harvesting, wherein the individual images or portions of video are linked to the crop attribute values detected by sensors 636. These values may be stored. The captured images or video are linked and indexed in a time-based manner or location-based manner to particular regions, individual rows or individual plants for which data is detected by sensors 636. As a result, when reviewing directly sensed crop attribute values (as detected by sensors 636) or derived crop attribute values for a particular region of a field, a particular set of rows of the field or a particular grouping of plants in the field, the operator may also retrieve and view images or videos of the actual region of the field, the particular rows of the field or the particular plants of the field corresponding to the data being viewed in a chart or map. Thus, system 620 allows an operator/monitor to visibly review the actual crops to either identify one or more conditions that may have affected the crop attribute such as yield or allows the operator/monitor to visibly confirm the crop/field condition identified by processor 630 as a reason for a particular crop yield or other attribute. For example, based upon data from sensors 636, processor 630 may output a conclusion that a drop in yield was caused by a wet spot in the field. Camera 637 permits the operator to pull up (from memory) actual stored video images of the particular portion of the field to confirm whether indeed the particular rows were in a wet spot.

In the example illustrated, system 620 offers several modes of operations for characterizer 623. In one mode, sensors 636 may be employed for crop characterization. In another mode, camera 637 may be employed for crop characterization. In yet another mode, both sensors 636 and camera 637 may be utilized for crop characterization. In some implementations, system 620 may omit one of sensors 636 or camera 637.

In some implementations, crop characterizer 623 may additionally comprise a local processor 639. Processor 639 receives signals from sensors 636 and conditions such signals prior to their transmission to on-board processor 630 via datalink 730. For example, in some implementations, processor 639 derives other crop attribute values from the signals prior to their transmission to processor 630. Processor 639 may filter such signals to reduce noise prior to transmission by link 730. In some implementations, processor 639 may trim data or compress data prior to transmitting such data across link 730 to processor 630 to reduce transmission and/or processing loads. In another implementation, processor 639 may be omitted.

On-board operator output 624 comprises one or more devices carried by harvester 622 by which information and data may be presented to an onboard operator of harvester 622. Output 624 may comprise a display comprising a monitor or screen with or without a speaker. On-board operator input 626 comprises one or more devices carried by harvester 622 by which selections and/or data may be input, entered and provided by a local operator 32 riding or operating harvester 622. Examples of input 626 include, but are not limited to, a keyboard, a touchpad, a touch screen, a steering wheel or steering control, a joystick, a microphone with associated speech recognition software and/or the like. In one implementation, input 626 may be provided as part of output 624 in the form of a touchscreen.

Localization input 627 comprises an input to processor 630 which provides geo-data to processor 630. In other words, input 627 provides location or positional information to processor 630. For example, in one implementation, localization input 627 may comprise a global positioning system (GPS) receiver. In other examples, other geo-data sources may be utilized.

Memory 628 comprises a non-transient computer-readable medium or persistent storage device for storing data for use by processor 630 or generated by processor 630. In one implementation, memory 628 may additionally store instructions in the form of code or software for processor 630. The instructions may be loaded in a random access memory (RAM) for execution by processor 630 from a read only memory (ROM), a mass storage device, or some other persistent storage. In other embodiments, hard wired circuitry may be used in place of or in combination with software instructions to implement the functions described. For example, at least regions of memory 628 and processor 630 may be embodied as part of one or more application-specific integrated circuits (ASICs). In the example illustrated, memory 628 is carried by harvester 622. In other implementations, memory 628 may be provided remote from harvester 622.

In the example illustrated, memory 628 comprises configuration module 650, correlation module 654 and condition detection module 656. Configuration module 650 comprises software code and associated stored data regarding the configuration of system 620. In the example illustrated, configuration module 650 includes sub-modules which direct processor 630 to prompt for selections from an operator, to store such selections and to operate according to such various selections. The stored selections control how processor 630 handles and analyzes data from characterizer 623 and how data or information is presented on output 624. In the example illustrated, configuration module 650 comprises interval sub-module 670, processing sub-module 672 and notification sub-module 674 which cooperate to present display screen 500 shown and described above with respect to FIG. 6. Interval sub-module 670 prompts for and stores operator input regarding how individual plants are to be aggregated such as the various aggregation technique prompts 502 in FIG. 6. Processing sub-module 672 prompts for and stores operator input regarding how such data is to be processed, for example, using statistical values such as average, median or range. Notification sub-module 674 prompts for and stores display settings such as with prompts 506 and 508 as well as prompts 510.

Correlation module 654 and condition detection module 656 comprise programming, software or code for directing the operation of processor 630. Correlation module 654 instructs processor 630 in the correlation of one or more directly sensed crop attribute values detected by sensors 36 to derived crop attribute values. In other words, correlation module 654 instructs processor 630 and the derivation of crop attribute values, such as yield and/or the like, from directly sensed crop attribute values or possibly along with other factors or inputs. In one implementation, correlation module 654 directs processor 630 to consult a lookup table in a database to correlate a stalk thickness/diameter as detected by sensors 636 to a grain mass or grain yield value, the derived crop attribute value. In another implementation, correlation module 654 directs processor 630 to carry out one or more algorithms/mathematical equations based upon a sensed impact of a plant or grain to derive a grain mass or yield of the plant. In other implementations, correlation module 654 may direct processor 630 to derived crop attribute values from directly sensed crop attribute values in other fashions.

Condition detection module 656 directs processor 630 in the identification of field and/or crop conditions based upon the directly sensed crop attribute values or the derived crop attribute values. Examples of such field and such are crop conditions include, but are not limited to, the absence of plants, a field washout condition, an area of the field having yields suffering from wheel compaction beyond a predetermined threshold, the existence of a weed patch, and the existence of yield loss due to inappropriate chemical application. In one implementation, condition detection module 656 directs processor 630 to consult a lookup table in the database to correlate a stalk thickness/diameter as detected by sensors 636 and/or a derived grain mass or grain yield value (the derived crop attribute value) to one of various predefined conditions, examples of which are set forth above. In another implementation, condition detection module 656 directs processor 630 to carry out one or more algorithms/mathematical equations using a directly sensed crop attribute value and/or a derived crop attribute value and to further compare the resulting calculation to one or more predefined thresholds to identify a field and/or crop condition. In other implementations, condition detection module 656 may direct processor 630 to identify or detect crop and/or field conditions in other fashions.

Static database 700 comprises a data storage containing data regarding historical or predefined data such as historical planting data, historical yield information, historical field or soil data (e.g., topography, soil type). Static database 700 may additionally contain tables and other information for correlating sensed crop attribute values to derived crop attribute values. Learned database 702 comprises a data storage containing data that varies as harvester 622 travels across the field. Database 702 stores the raw directly sensed crop attribute values from sensors 636 and/or camera 637, camera captured video or images, derived crop attribute values, and varying or adjustable harvester operational parameters, for example, harvester velocity, head height, and other harvester settings. In one example, database 702 further stores GPS data.

In the example illustrated, static database 700 and learned database 702 comprise databases that are part of memory 628 on board harvester 622. In other implementations, such databases 700, 702 may be remote from harvester 622 and may be accessed through communication 706. Online database 704 comprises a database that is accessed through a wide area network or a local area network using communication 706. Online database 704 may contain additional information for use by processor 630 and harvester 622. Communication 706 comprises a communication network facilitating communication between harvester 622 and remote entities such as online database 704, office 708, service provider 710, other on-site machines 712 and remote operator/observer 714.

Enterprise back office 708 comprises a location remote from harvester 622 such as the home farm. Enterprise back office 708 may include computing devices and a database, wherein processor 630 transmits data stored in learned database 702 to office 708 through communication 706 for backup and/or remote analysis. Third-party service provider 710 comprises a server in communication with harvester 622 through communications 706 and associated with a third-party such as an agronomist, a seed dealer, a seed company, a chemical, insecticide or fertilize supplier or third-party data storage host.

As indicated by FIG. 8, other harvesters or other machines on a particular worksite or field may also be in communication with harvester 622 through communications 706. As a result, sensed crop data may be shared amongst such multiple machines on a particular field or worksite. In some implementations, harvester 622 may communicate with the remote operator/observer 714 through communications 706. As a result, harvester 622 may be remotely controlled (the steering of harvester 622 and/or the adjustment of settings for the operation of crop sensing by harvester 622).

Figure 9:
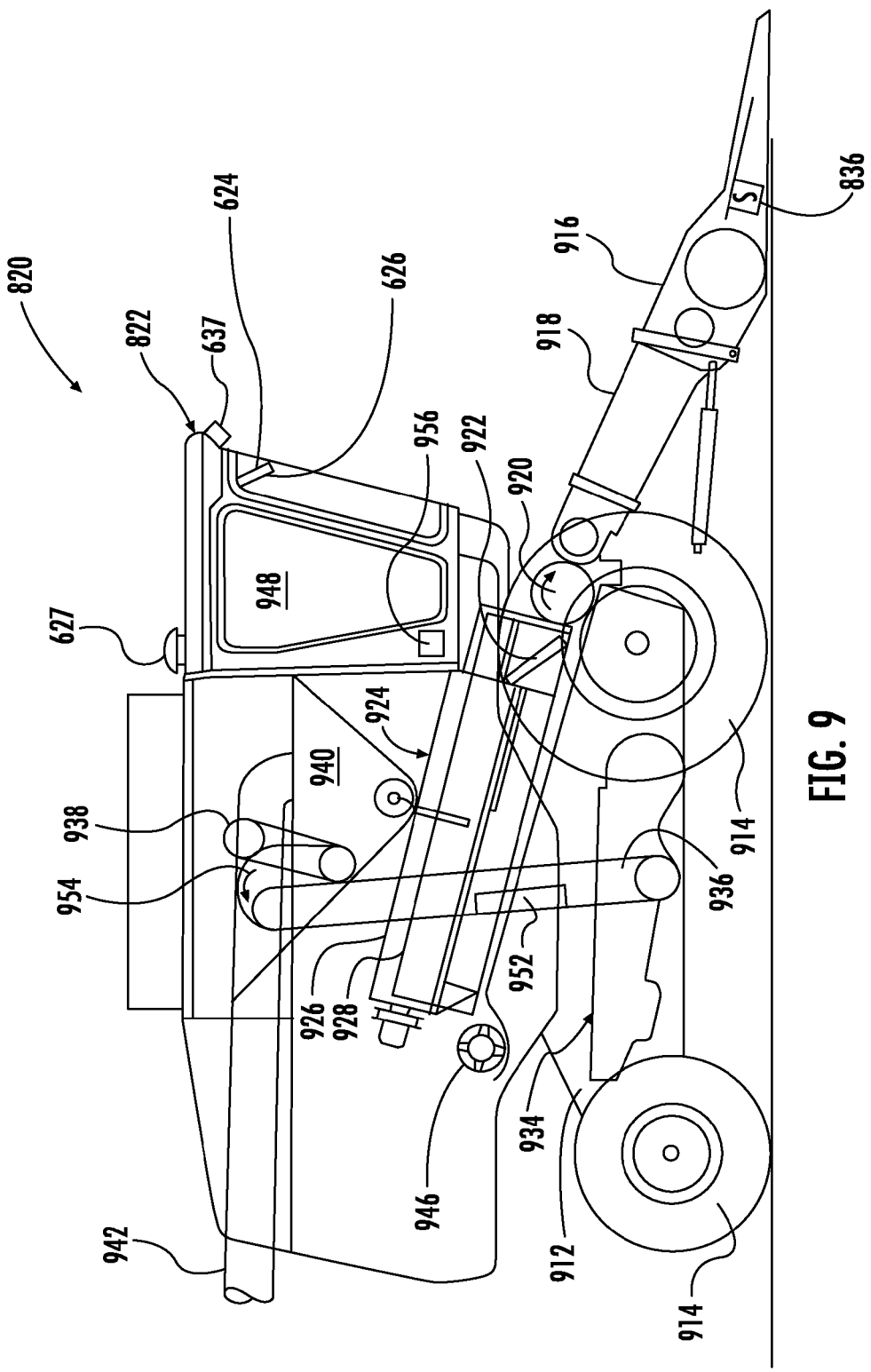
FIG. 9 is a side elevational view of an example crop sensing system comprising the crop sensing system of FIG. 8.

FIGS. 9 and 10 illustrate crop sensing system 820, an example of crop sensing system 20 or an example of crop sensing system 620. In the example illustrated, crop sensing system 820 comprises a harvester 822 (in the form of a combine). Crop sensing system 820 comprises each of the components illustrated and described with respect to FIG. 8, some of which are shown and similarly numbered in FIG. 9, except that crop sensing system 820 specifically includes sensors 836, particular examples of sensors 636.

Harvester 822 comprises a chassis 912 which is supported and propelled by ground engaging wheels 914. Although harvester 822 is illustrated as being supported and propelled on ground engaging wheels 914 it can also be supported and propelled by full tracks or half-tracks. A harvesting assembly 916 (shown as a corn head) is used to take up crop and to conduct it to a feeder house 918. The crop is conducted by the feeder house 918 to a beater 920. The beater 920 guides the crop upwardly through an intake transition region 922 to a rotary threshing and separating assembly 924. Although harvester 822 is described as a rotary combine, in other implementations, harvester 822 may comprise other types of combines (for example combines having a transverse threshing cylinder and straw walkers or combines having a transverse threshing cylinder and rotary separator rotors) or other agricultural harvesting machines including, without limitation, self-propelled forage harvesters, sugar cane harvesters, and windrowers The rotary threshing and separating assembly 924 comprises a rotor housing 926 and a rotor 928 arranged in the rotor housing 926. The harvested crop enters the rotor housing 926 through the intake transition region 922. The rotary threshing and separating assembly 924 threshes and separates the harvested crop. Grain and chaff fall through grates at the bottom of the rotor housing onto a cleaning assembly 934. The cleaning assembly 934 removes the chaff and conducts the clean grain to a grain elevator 936 which conducts upwardly to a distributing screw conveyor 938. The distributing screw conveyor 938 deposits the clean grain in a grain tank 940. The clean grain in the grain tank 940 can be unloaded through an unloading auger 942 into a trailer or truck. Threshed straw separated from the grain is conducted out of the rotary threshing and separating assembly 924 through an outlet to a discharge beater 946. The discharge beater 946 ejects the straw out the rear of harvester 822.

The operation of harvester 822 is controlled from an operator's cab 948. In the illustrated embodiment, localization input 627 (a geographic position sensor in the form of a receiver) for the reception of GPS signals (global positioning system) is attached above the operator's cab 948. A speed sensor measuring the speed of the wheels 914 may be provided. Mounted on one side of the clean grain elevator 936 is a capacitor moisture sensor 952 for measuring the moisture content of the clean grain. Such a sensor is disclosed in DE 199 34 881 A., the full disclosure of which is hereby incorporated by reference. A mass flow sensor 954 is located at the outlet of the clean grain elevator 936. The mass flow sensor 954 comprises an impeller plate mounted for rotation about a horizontal axis. Its deflection is dependent upon the mass flow rate of the clean grain. The deflection of the impeller plate is measured and thus data on the mass flow rate of the harvested grain is provided. Such a sensor is described in EP 0 853 234 A (the full disclosure of which is hereby incorporate by reference) and the documents recited therein.

Sensors 836 are similar to sensors 636 in that sensors 836 comprise mechanisms to concurrently sense or detect one or more crop attribute values for multiple portions of a utilized crop harvesting width of the harvester. Said another way, each of sensors 836 senses only a portion of the total crop being harvested at any moment in time by the harvester 822, wherein each of sensors 836 provide crop attribute values for just that portion. In one implementation, sensors 836 provide crop attribute values on a row-by-row basis. In another implementation, sensors 836 provide crop attribute values on a plant-by-plant basis or based upon an aggregation of individual plants. Such crop attribute values for the individual plants do not merely comprise of data regarding the population of plants or the spacing of plants. Instead, each of sensors 836 are configured to specifically sense other attributes of the individual plant such that crop attribute values pertaining to estimated mass of the grain or product of the individual plant, the estimated mass other than grain (MOG) of the plant and/or the like may be derived.

As further shown by FIG. 9, crop sensing control unit 956 is located in the operator's cab 948 or somewhere else on the harvester 822. Crop sensing control unit 956 comprises each of memory 628, processor 630 and databases 700, 702 described above with respect to FIG. 8. Crop sensing control unit 956 is in communication with localization input 627, the moisture sensor 952, the mass flow sensor 954, the speed sensor, when present, and sensors 836. Crop sensing control unit 956 is provided with an internal clock or receives external time signals, for example from the input 627. Crop sensing control unit 956 records the amount of harvested grain, measured by means of the mass flow sensor 954, and its moisture content, measured by means of the moisture sensor 952, dependent on the geographical position of the harvester 822 (measured by means of the localization input 627, e.g., a GPS receiver. Crop sensing control unit 956 additionally receives signals and/or data from sensors 836 and derives one or more crop attribute values for each of multiple distinct portions of harvesting platform 916. In one implementation, crop sensing control unit 956 derives one or more crop attributes for individual rows or road units of harvesting platform 916, wherein data is processed and stored on a row-by-row basis. In another implementation, crop sensing control unit 956 derives and stores one or more crop attributes for individual plants or aggregations of individual plants. Crop sensing control unit 956 logs the data in learned database 702 and produces a field summary which may also be stored in learned database 702 and presented on output 624. In one implementation, crop sensing control unit 956 creates a yield map, similar to either of maps 300 or 400 shown in FIGS. 4 and 5, respectively.

FIG. 10 schematically illustrates an example operation of sensors 836 and crop sensing control unit 956. As shown by FIG. 10, in one implementation, sensors 836 are mounted to or within harvesting platform 916 (shown as a corn head). In one implementation, sensors 836 comprise accelerometers, strain gauge sensors and/or the like mounted to or coupled to at least one stripper plate 980 along multiple row units of harvesting platform 916. In one implementation, sensors 836 are mounted to or couple to at least one stripper plate 980 along each row unit of harvesting platform 916. Sensors 836 are in communication with processor 630 of crop sensing control unit 956 (shown in FIG. 9). In one implementation, one sensor is associated with one row unit. In other implementations, more than one sensor may be associated with one row unit. In such a case, the sensors may be of the same type sensing the same or different attributes, or of different types sensing the same or different attributes. In yet other implementations, one sensor may be associated with multiple row units.

FIG. 11 is a flow diagram of an example method 1000 by which crop sensing control unit 956 may determine or derive one or more crop attribute values using signals from sensors 836. As indicated by block 1002, processor 630 receives signals from sensors 836 sensing the interaction, such as contact or movement, of the crop with or with respect to the head or harvesting platform 916. In the example illustrated in which harvesting platform 916 comprises a corn head, processor 630 receive signals from sensors 836 that are coupled to at least one stripper plate 980 of each row unit, wherein sensors 836 sense an impact of an ear 984 of corn upon the one or more stripper plates 980 along a row unit. As indicated by block 1004, based at least upon this sensed interaction, i.e., the impact of the ear 984 of corn upon the one or more stripper plates 980, processor 630 derives a secondary crop attribute value, such as yield. As indicated by block 1006, processor 630 stores and/or displays the secondary crop attribute value. Although processor 630 is described as receiving signals from sensors 836 which are illustrated as being coupled to stripper plates so as to sense interaction of ear 984 with stripper plates 980, in other implementations, processor 630 may receive crop interaction signals from sensors 836 mounted at other locations to sense other interactions of the plant or its grain product with harvesting platform 916.

FIG. 12 is a flow diagram of method 1050, a specific implementation of method 1050 by which crop sensing control unit 956 may determine or derive one or more crop attribute values using signals from sensors 836. As indicated by block 1052, processor 630 receives signals from sensors 836 sensing a pulse of ear impact upon stripper plate 980. As indicated by block 1054, processor 630 further determines the velocity component of the ear 984. Such a velocity may be determined based at least in part upon the velocity of harvester 822 as it moves in the direction indicated by arrow 988. This velocity may be obtained from the aforementioned speed sensor or from localization input 627. As indicated by block 1056, processor 630 divides the sensed pulse by the determined velocity to estimate a mass of the individual ear 984.

As indicated by block 1058, processor 630 may then derive the crop attribute, such as yield, for ear 984 based upon the determined mass of ear 984. In one implementation, processor 630 may consult a lookup table, such as contained in database 700, to derive a grain yield for ear 984. Using such information, processor 630 may also determine a yield for the individual plant. Based upon the spacing in time between consecutive pulses provided by sensor 836, processor 630 may determine whether consecutive pulses are the product of two ears on a single plant or two ears on separate plants. As a result, processor 630 may determine the yield for the individual plant. Results for individual plants may be aggregated (as described above) or may not be distinguished from one another along a row to output yield on a row-by-row basis. As indicated by block 1068, the derived crop attributes, such as yield, may be stored in learned database 702 and/or may be presented on output 624.

Figure 13:
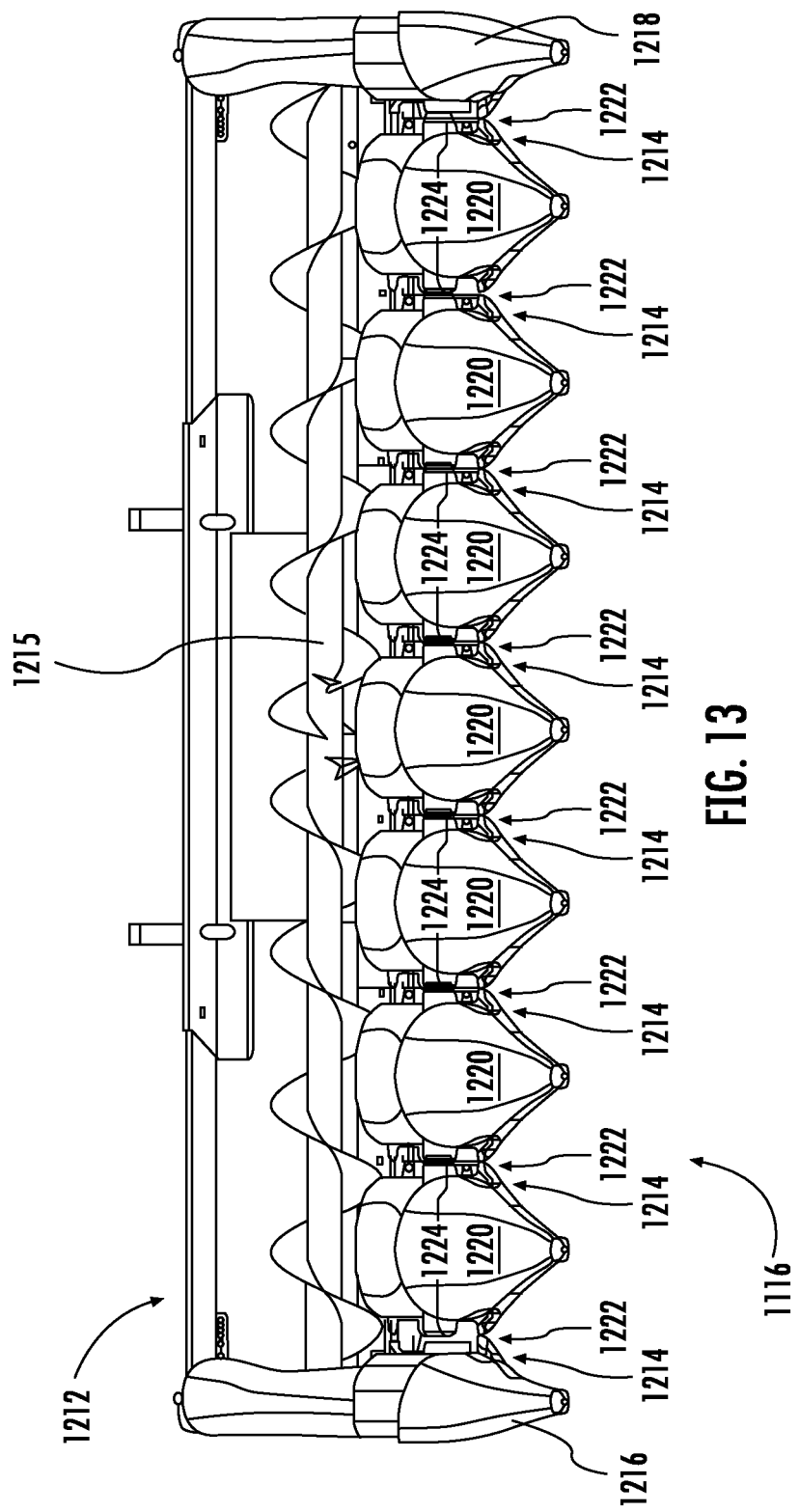
FIG. 13 is a front elevational view of an example harvesting platform for the crop sensing system of FIG. 9.
Figure 14:
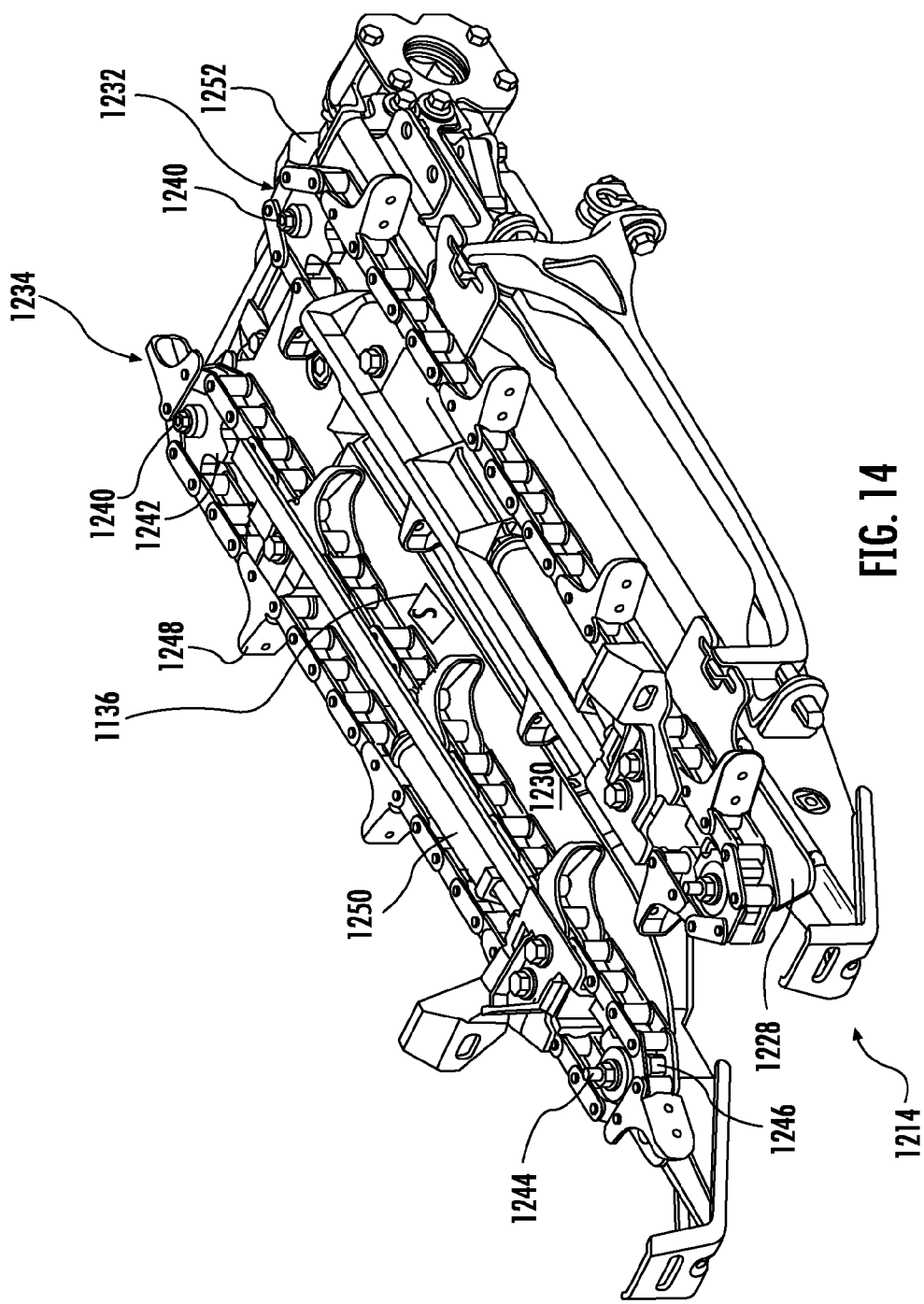
FIG. 14 is a top perspective view of an example row unit of the harvesting platform of FIG. 13.

FIGS. 13-16 illustrate harvesting platform 1116 (shown as a corn head) and sensors 1136, shown in FIG. 14, examples of harvesting platform 916 and sensors 836 described above. As shown by FIG. 13, harvesting platform 1116 comprises a frame 1212, row units 1214, auger 1215, outer dividers 1216, 1218 and central dividers 1220. Frame 12 extends across the physical width of harvesting platform 1116 and supports row units 1214. Row units 1214 harvest corn from individual rows of crop and convey the harvested corn to auger for further conveyance into harvester 1212. Row units 1214 are spaced in a side-by-side relationship with each other a distance commensurate with the spacing between adjacent rows of corn to be harvested. In some implementations, the row units 1214 may be adjustable to accommodate other corn row spacings. Outer dividers 1216, 1218 and central dividers 1220 separate co-mingled stalks of adjacent rows from one another. Central dividers 1220 extend between consecutive row units 1214. Dividers 1216, 1218 and 1220 cooperate to define longitudinal passages 1222 which are centered relative to the rows to be harvested and a fore-and-aft extending relatively narrow throat 1224 defined by each row unit 1214.

Figure 15:
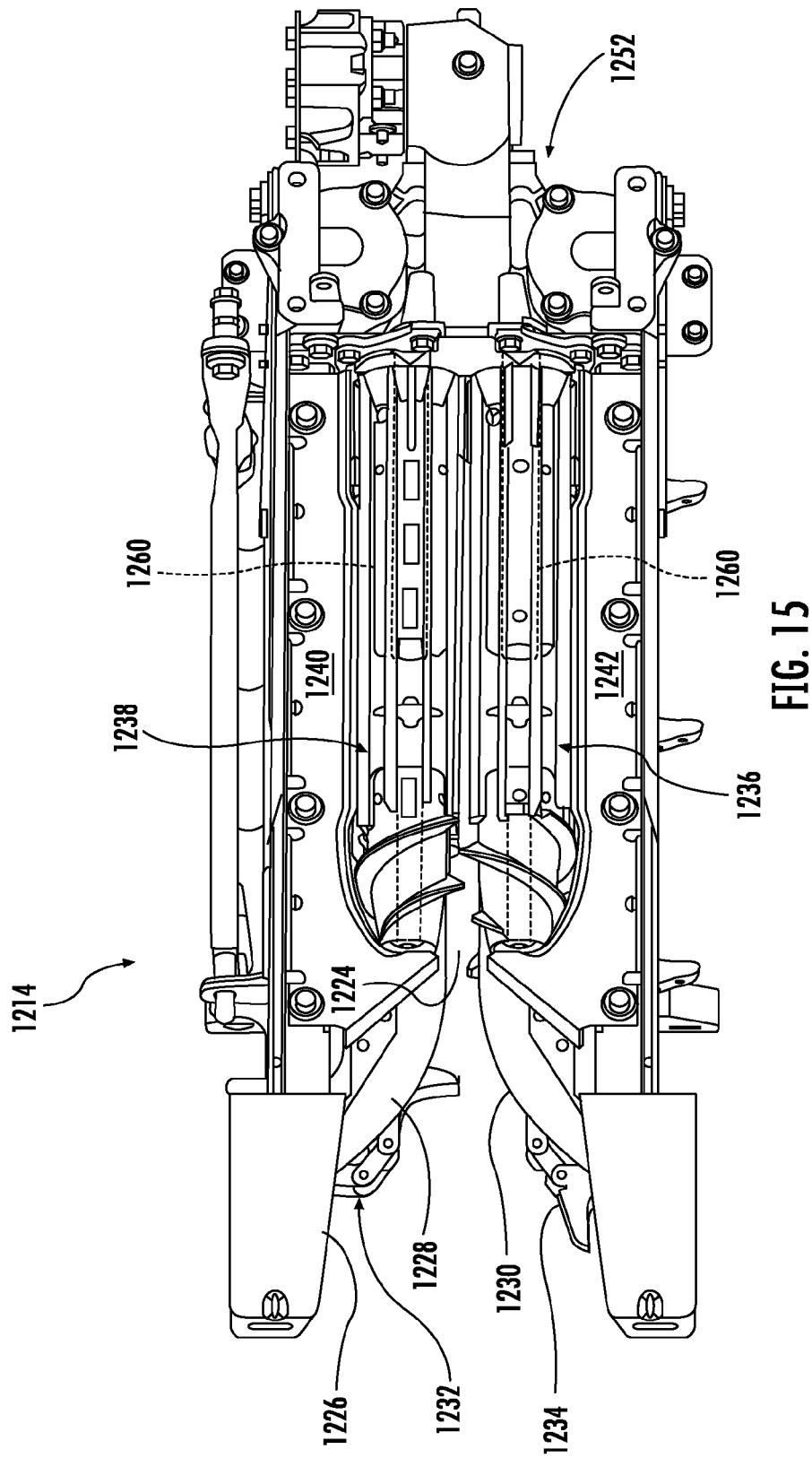
FIG. 15 is a bottom perspective view of the row unit of FIG. 14.
Figure 16:
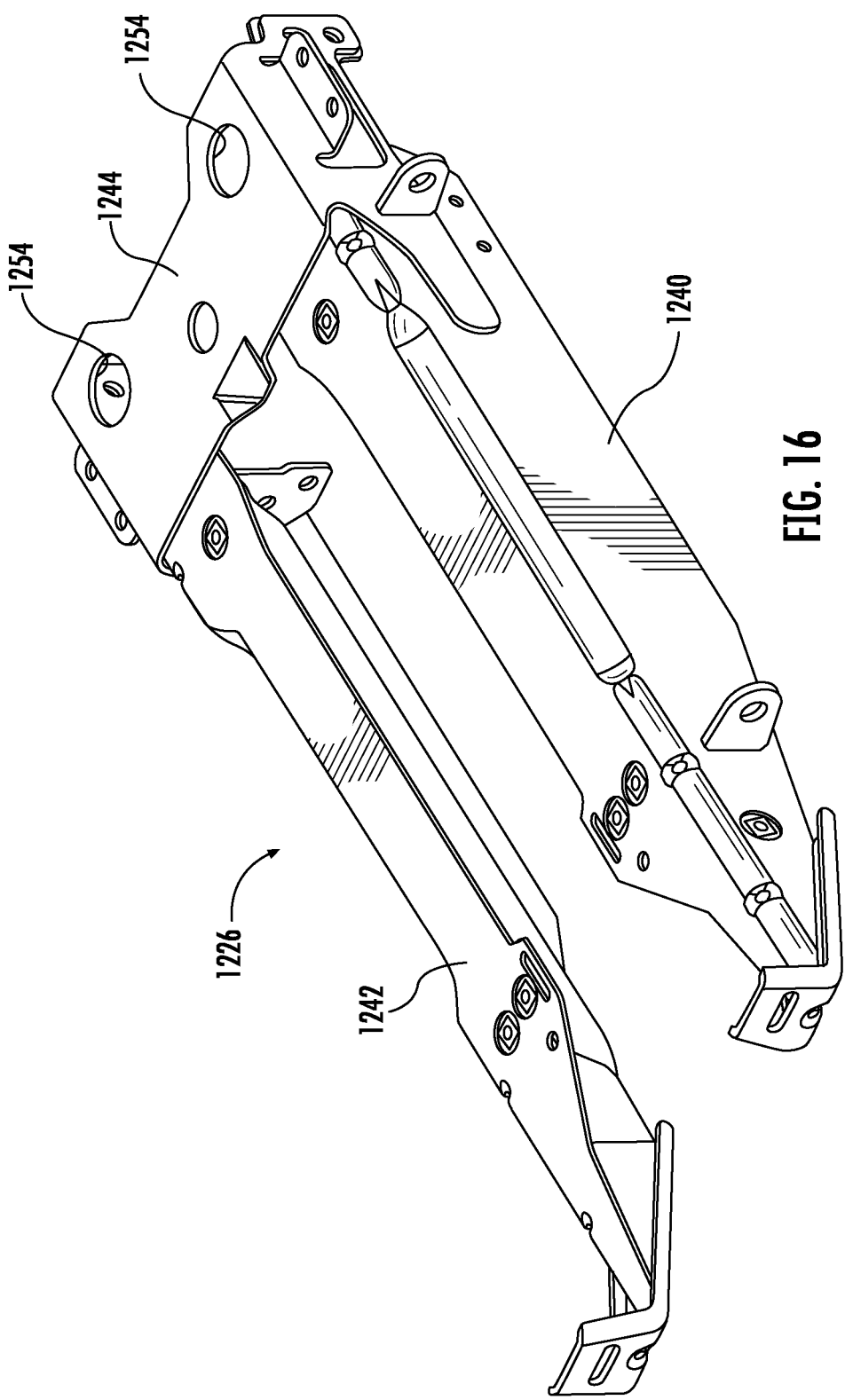
FIG. 16 is a top perspective view of an example frame of the row unit of FIGS. 14 and 15.

FIGS. 14-16 illustrate one example of a row unit 1214 in more detail. As shown by FIGS. 14-16, in addition to sensor 1136, each row unit 1214 comprises frame 1226, right and left stripper plates, also known as deck plates, 1228, 1230, right and left gathering units 1232, 1234 and snapping rolls 1236, 1238 (shown in FIG. 15). As shown by FIG. 16, frame 1226 comprise a U-shaped member having right and left, fore and aft extending legs 1240, 1242 interconnected by a transversely extending bracket or bight 1244. Legs 1240, 1242 support stripper plates 1228, 1230 as well as right and left gathering units 1232, 1234 and snapping rolls 1236, 1238.

Stripper plates 1228, 1230 comprise plates having inner edges spaced apart so as to define narrow throat 1224. Throat 1224 receives cornstalks of an aligned row as row unit 1214 moves along a row of crops. As row unit 1214 is moved along the row, the stalks are drawn down through throat 1224 with the assistance of snapping rolls 1236, 1238 (shown in FIG. 15) such that ears of corn carried by the stalk impact the stripper plates and are separated from the stalk. Such stripper plates 1228, 1230 may include elongated openings for receiving fasteners such that stripper plates 1228, 1230 may be laterally adjusted to adjust the width or size of throat 24. As noted above, in some implementations, an actuator may be coupled to stripper plates to automatically adjust the spacing a stripper plates 1228, 1230 in response to control signals from processor 630 based upon sensor derived crop attribute values for the particular row unit 1214.

In the example illustrated, at least one sensor 1136 (schematically shown), such as a accelerometer or strain gauge is mounted to an underside of at least one of stripper plates 1228, 1230 to sense the impact of the ear of corn upon stripper plates 1228, 1230. As discussed above with respect to sensors 836 and a method 1050, signals produced by sensor 836 are used by processor 630 to ultimately derive a mass of the particular ear corn that has impacted stripper plates 1228, 1230 as well as to derive the yield from the particular ear of corn.

Right and left gathering units 1232, 1234 gather the ears of corn and transport such ears rearwardly towards auger 1215 (shown in FIG. 13). In the example illustrated, each of gathering units 1232, 1234 comprises driveshaft 1240, drive sprocket 1242, idler shaft 1244, idler sprocket 1246, gathering chain 1248, and chain tensioning assembly 1250. Each of drive shafts 1240 extends from and is driven by a gearbox 1252 to rotationally drive sprocket 1242. Each of drive shafts 1240 extends through a corresponding opening 1254 in bight 1244 of frame 1226 (shown in FIG. 16). Drive sprockets 1242 cooperate with idler sprockets 1246 to support and drive gathering chain 1248.

Idler shafts 1244 are rotationally supported by chain tensioning assemblies 1250. Idler shafts 1244 rotationally support idler sprockets 1246. Chain tensioning assemblies 1250 adjustably support idler sprockets 1246 for movement between different fore and aft positions to adjust the tension of gathering chains 1248. Snapping rolls 1236, 1238 are mounted to a pair of drive shafts 1260 with project forwardly from gearbox 1252. As noted above, snapping rolls 1236, 1238 draw cornstalks down through throat 1224, between stripper plates 1228, 1230. Because ears of corn are too large to pass down through throat 1224, such ears impact stripper plates 1228, 1230 and are detached or severed from the stalks for being gathered by gathering chains 1248.

Although the present disclosure has been described with reference to example embodiments, workers skilled in the art will recognize that changes may be made in form and detail without departing from the spirit and scope of the claimed subject matter. For example, not everything feature shown in drawings is required and one or more features may be omitted. Although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described with reference to the example embodiments and set forth in the following claims is manifestly intended to be as broad as possible. For example, unless specifically otherwise noted, the claims reciting a single particular element also encompass a plurality of such particular elements.

What is claimed is:

1. An apparatus comprising:
a harvester comprising a movable stripper plate;
an actuator to adjust positioning of the movable stripper plate based upon at least one of sensed crop attribute values or derived crop attribute values;
a first row unit comprising the movable stripper plate, a first sensor associated with the first row unit and the actuator, wherein the actuator is to automatically move the stripper plate based upon signals from the first sensor; and
a second row unit comprising a second movable stripper plate, a second sensor associated with the second row unit and a second actuator, the second actuator to automatically move the second stripper plate based upon signals from the second sensor, wherein the second actuator is to move the second stripper plate of the second row unit independent of movement of the stripper plate of the first row unit to provide the first row unit and the second row unit with different stripper plate spacings, wherein the actuator is to automatically move the stripper plate based upon a first determined grain yield value associated with the first row unit and wherein the second actuator is to automatically move the second stripper plate based upon a second determined grain yield value, different than the first determined grain yield value, associated with the second row unit.

2. The apparatus of claim 1, wherein with different stripper plate spacings are concurrently provided by the actuator and the second actuator.

3. The apparatus of claim 1, wherein the first grain yield value is based upon sensed interactions of a crop with the movable stripper plate and wherein the second grain yield value is based upon sensed interactions of the crop with the second movable stripper plate.

4. The apparatus of claim 1, wherein the first grain yield value is based upon sensed interactions of an ear of corn with an upper surface of the movable stripper plate and wherein the second grain yield value is based upon sensed interactions of an ear of corn with an upper surface of the second movable stripper plate.

5. The apparatus of claim 1 further comprising a processing unit, wherein the processing unit is to determine attribute of the crop comprises a mass of an ear individual ears of corn, wherein the first grain yield value and the second grain yield value are based upon the determined mass of the individual ears of corn.

6. An apparatus comprising:
a first row unit;
a second row unit;
a processor to determine a first grain yield value for the first row unit and a second grain yield value for the second row unit different than the first grain yield value;
the first row unit comprising a first movable stripper plate and an actuator, wherein the actuator is to automatically move the first stripper plate based upon the first grain yield value associated with crops harvested by the first row unit; and the second row unit comprising a second movable stripper plate and a second actuator, the second actuator to automatically move the second stripper plate based upon the second grain yield value associated with crops harvested by the second row unit, wherein the second actuator is to move the second stripper plate of the second row unit independent of movement of the first stripper plate of the first row unit to concurrently provide the first row unit with a first stripper plate spacing and the second row unit with a second stripper plate spacing different than the first stripper plate spacing.

7. The apparatus of claim 6, wherein the first grain yield value is based upon sensed interactions of a crop with the stripper plate and wherein the second grain yield value is based upon sensed interactions of the crop with the second stripper plate, wherein the second actuator is to move the second stripper plate of the second row unit independent of movement of the stripper plate of the first row unit to provide the first row unit and the second row unit with different stripper plate spacings.

8. The apparatus of claim 6, wherein the first grain yield value is based upon sensed interactions of an ear of corn with an upper surface of the stripper plate and wherein the second grain yield value is based upon sensed interactions of an ear of corn with an upper surface of the second stripper plate.

9. The apparatus of claim 6 further comprising a processing unit, wherein the processing unit is to determine attribute of the crop comprises a mass of an ear individual ears of corn, wherein the first grain yield value and the second grain yield value are based upon the determined mass of the individual ears of corn.

10. An apparatus comprising:
a harvester comprising:
 a first portion having first stripper plates;
 a second portion having second stripper plates; and
 at least one actuator to move the first stripper plates and the second stripper plates; and
a non-transitory computer-readable medium storing computer-readable code to direct a processing unit to:
receive a sensed metric of a crop being harvested by the a harvester; and
determine a first grain yield value for the a first portion and a second grain yield value, different than the first grain yield value, for the a second portion of the harvester based upon the sensed metric;
determine a first stripper plate spacing for the first stripper plates of the first portion based upon the determined first grain yield for the first portion;
determine a second stripper plate spacing for the second stripper plates of the second portion, different than the first stripper plate spacing, based upon the determined second grain yield of the second portion; and
output control signals directing the to direct at least one actuator to provide the first stripper plates of the first portion with the determined first stripper plate spacing and to provide the second stripper plates of the second portion with the determined second stripper plate spacing.

11. The apparatus of claim 10, wherein the code is to further to direct the processing unit to automatically output control signals to direct an actuator to automatically provide the first portion with the first stripper plate spacing and the second portion with the second stripper plate spacing.

12. The apparatus of claim 10, wherein the first portion comprises a first row unit and wherein the second portion comprises a second row unit.

13. The apparatus of claim 10, wherein the sensed metric comprises an interaction of the crop being harvested with stripper plates of the first portion and the second portion.

14. The apparatus of claim 10, wherein the harvester comprises a head and wherein the sensed metric results from interaction of the crop with the head.

15. The apparatus of claim 10, wherein the harvester comprises a head and wherein the sensed metric comprises a force of the crop impacting the head.

16. The apparatus of claim 10, wherein the harvester comprises a head and wherein the sensed metric comprises a force of grain impacting the head.

17. The apparatus of claim 10, wherein the harvester comprises a cornrow head having stripper plates against which ears of corn impact to separate from corresponding stalks, wherein the sensed metric is produced from the ears impacting the stripper plates.

18. The apparatus of claim 10, wherein the sensed metric comprises a force of the ears impacting stripper plates.

19. The apparatus of claim 10, wherein the code is to further direct the processing unit to determine a mass of individual ears of corn, wherein the first grain yield value and the second grain yield value are based upon the determined mass of the individual ears of corn.

* * * * *